United States Patent [19]

Shahinian, Jr.

[11] 4,324,044

[45] Apr. 13, 1982

[54] SURGICAL KNIFE FOR PRECISE DEPTH OF CUT CONTROL

[76] Inventor: Lee Shahinian, Jr., 1232 Lisa La., Los Altos, Calif. 94022

[21] Appl. No.: 174,754

[22] Filed: Aug. 4, 1980

[51] Int. Cl.³ .................................................. B26B 29/02
[52] U.S. Cl. ........................................ 30/294; 128/305
[58] Field of Search ................. 30/287, 294, 353, 293, 30/320, 286; 128/305, 314

[56] References Cited

U.S. PATENT DOCUMENTS

| | | | |
|---|---|---|---|
| 3,892,038 | 7/1975 | Novak | 30/294 |
| 3,898,735 | 8/1975 | Himeno | 30/294 |
| 3,967,377 | 7/1976 | Wells | 30/320 |

FOREIGN PATENT DOCUMENTS 194892  3/1923  United Kingdom ................. 30/293

Primary Examiner—Jimmy C. Peters
Attorney, Agent, or Firm—Allston L. Jones; David A. Boone

[57] ABSTRACT

A surgical knife assembly in which the handle portion tapers down and is truncated obliquely at a selected angle to form a blade guard surface. The blade of this knife has a dull edge and a sharpened edge which meet in a point with an acute included angle. This blade is affixed to the blade guard surface so that the dull edge of the blade intersects the straight edge of the blade guard surface with the side portions of the blade being perpendicular to that same straight edge. In addition, when the blade is affixed to the blade guard surface, the dull edge of the blade is mounted so that it is substantially parallel to the major axis of the handle. To insert the blade in the surface where the incision is to be made, the knife is designed so that the user will hold the surgical knife so that the guard surface is substantially parallel to the surface to be cut. By orienting the knife in this way, the point of entrance of the knife is clearly visible and the blade guard surface will limit the initial depth of cut by preventing the handle of the knife from following the blade into the incision. Once in place, the user continues the incision by drawing the knife toward them by bending the fingers at the same time maintaining the straight edge of the guard surface in contact with the surface in which the incision is being made. By maintaining this contact between the surface being cut and the straight edge the depth of the incision continues to be limited since this straight edge extends to either side of the blade and acts as a pivot point around which the handle of the knife rotates as the knife is drawn toward the user.

4 Claims, 6 Drawing Figures

SURGICAL KNIFE FOR PRECISE DEPTH OF CUT CONTROL

BACKGROUND OF THE INVENTION

The present invention relates to surgical knives for making a controlled depth of cut and more particularly to knives for ophthalmic surgery where the control of the depth of cut can be critical to achieving the desired surgical result.

Many surgical procedures require that the depth of cut be controlled and surgery on the eye is one area where these procedures and the depth of cut are most critical. A controlled partial thickness (lamellar) eye wall incision is often needed for cataract surgery, peripheral iridectomy, glaucoma filtering surgery, lamellar keratectomy, radial lamellar corneal incisions for correction of myopia, retinal detachment surgery and other procedures. Without a knife that is capable of making a controlled depth incision the surgeon must free-hand the depth of the lamellar incision. This is particularly dangerous in that if the incision becomes too deep, vitreous or aqueous fluid may leak from the eye and intraocular structures may be damaged, resulting in possible blindness.

By using the free-hand depth of control method, it is often necessary for the surgeon to go back over an incision gingerly and repeatedly to achieve the desired depth of cut. Such multiple passes with the knife are time consuming, create a more ragged wound and distract the surgeon from the proper incision location. Additionally, as the surgeon draws the knife blade through the tissue and toward himself by bending the fingers, the angle of the leading edge of the knife handle to the tissue being cut becomes less acute. Alternately, when the incision is made by pushing the blade away from the surgeon by extending the fingers, the angle of the leading edge of the knife handle to the tissue being cut increases beyond 90°. In either of these instances the depth of cut can vary drastically. Ideally, the knife should maintain a relatively uniform depth of cut throughout the entire incision despite the changes in the angle of the handle and the blade itself to the tissue being cut.

One type of surgical knife in common usage for making eye wall incisions consists of a simple cylindrical plastic handle which tapers down to a rounded tip having a diameter of approximately 2 millimeters. A sharpened steel blade is embedded in the rounded tip and extends approximately 2 millimeters from the rounded plastic tip of the knife handle. This type of knife is designed for surgical procedures requiring a controlled depth of cut. However, for making eye wall incisions the blade extends much further beyond the tip of the handle than the 0.5 millimeters average cut depth for lamellar eye wall incisions. Thus, the surgeon must rely on the free-handing techniques that he has developed in previous operations. In other surgical procedures where a 2 millimeter depth of cut is acceptable, the free-handed method must still be relied upon since the rounded tip of the handle may not be an acceptable blade guard, i.e., it may follow the blade into the incision.

A second type of surgical knife in common usage is the Beaver knife disclosed in U.S. Pat. No. 4,074,431 entitled "Surgical Knife Assembly, Surgical Blade and Method of Manufacture Thereof." The blades in this knife are thin (approximately 0.1 millimeters) allowing for fine incisions with a minimal amount of pressure and pointed to allow easy entry into the tissue. However, these knives have the same shortcomings as the one discussed above in that the blade is not guarded to afford a controlled lamellar depth of cut.

A guarded surgical knife is disclosed in U.S. Pat. No. 3,945,117 entitled "Surgical Blade With Adjustable Blade Guard." The design disclosed in this patent presents several problems in application. As the knife is angled away from the vertical position either by the surgeon drawing it toward him or pushing it away, the bearing surfaces of the guard rest against the surface being cut with the depth of cut varying by approximately 20%. In addition, the plastic blade guard projects beyond the leading and trailing edges of the blade thus reducing visibility of the blade and the surface being cut. In this knife, the blade is relatively thick (approximately 0.6 millimeters) in its flat portion. If this blade were used for making a lamellar incision of 0.5 millimeters in depth, the width of the incision would approach its depth, creating an undesirable furrow effect. Furthermore, the blade is not pointed, preventing easy entry at a precise location. Finally, since the knife is not preassembled and ready to use, the four components (blade, guard, handle, and guard adjuster) must be manipulated to adjust the extension of the blade from the end of the blade guard to provide the desired depth of cut. This manipulation is very time consuming considering that for eye surgery one normally is dealing with tolerances of 0.1 millimeters.

It would be desirable to have a surgical knife for making eye wall incisions wherein the blade is less than 0.2 millimeters thick at its thickest point, the blade being preset into a handle designed to provide a maximum of 10% depth of cut variation as the knife is pushed away from or pulled toward the surgeon, there is a built-in blade guard to ensure that the depth of cut does not vary more than the desired 10%, and that visualization of the blade is maximized during the surgery. The surgical knife of the present invention achieves each of the above desired results.

SUMMARY OF THE INVENTION

In accordance with the illustrated embodiment, the present invention provides a surgical knife with good visibility of the surface being cut and for controlling the depth of the incision as well as the variations in the incision depth. The surgical knife of the present invention includes a handle means and a blade means. The handle means is selectively truncated obliquely to the major axis of the handle on its tapered end forming a guard surface with a normal vector to the guard surface forming an angle α to the major axis of the handle means. The blade means is affixed substantially perpendicular to the guard surface and extends outward therefrom. In addition, the blade means has a dull edge, and a sharpened edge with the intersection of these two edges forming the point of maximum extent of the blade means from the guard surface of the handle means with an acute included angle between these edges of the blade means.

The guard surface of the handle means is substantially flat and has at least one straight side. This guard surface limits the ability of the knife to follow the blade into the incision and thus limits the depth of the initial cut. In addition this guard surface assists the user in orienting the surgical knife with its major axis at an angle α to the surface to be cut, thus improving visibility of the point of entry of the blade into that surface. The portion of the blade means extending from the guard surface is positioned such that its dull edge intersects the at least one straight side of the guard surface substantially in its center with the side surfaces of the blade means being substantially perpendicular to the at least one straight side. As the user draws the surgical knife toward him the portions of the at least one straight side of the guard means extending laterally from each side of the blade means remain in contact with the surface being cut and thus limit the depth of the incision.

With this configuration the surgical knife has a maximum depth of cut that is substantially equal to the exposed length of the dull edge of the blade means. Similarly, the minimum depth of cut for a surgical knife of this configuration is substantially equal to the exposed length of the dull edge of the blade means multiplied by the COS of the angle $\alpha$. Therefore, if the angle $\alpha$ is selected to be substantially equal to 25°, a resultant difference between the maximum and minimum depths of cut will be substantially equal to 1/10th the exposed length of the dull edge of the blade means.

DESCRIPTION OF THE PREFERRED EMBODIMENT

Figure 1:
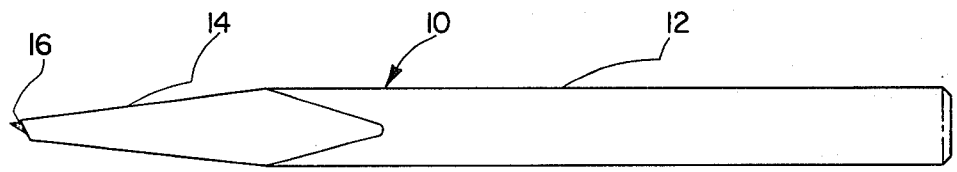
FIG. 1 is a plane view of the surgical knife of the present invention.

Referring to FIG. 1 there is shown a surgical knife 10 of the present invention which includes a handle portion 12, a blade holding portion 14 and blade 16. Handle portion 12 and blade holding portion 14 can be made of any suitable material including any one of several rigid plastic materials. If a plastic material is used then handle portion 12 and blade holding portion 14 can be molded as a common piece with blade 16 being precisionally inserted into the mold prior to the insertion of the plastic material. A typical knife of this type will be approximately 100 millimeters long and have a handle portion 12 that is approximately 6 millimeters in diameter with blade holding portion 14 tapering toward blade 16 to provide greater visibility during the surgical procedure. For such a knife to be useful, the handle must be large enough in diameter to be held comfortably and short enough to provide the ease of use under an operating microscope. The above dimensions meet these objectives.

Figure 2:
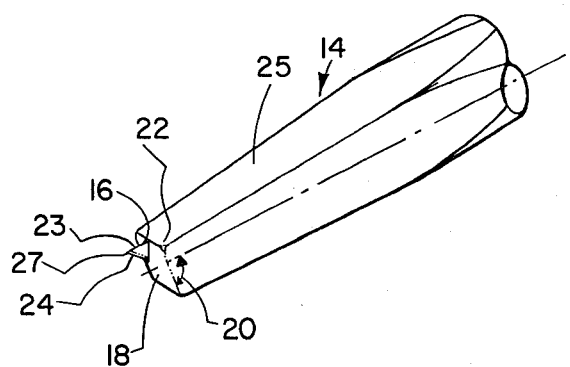
FIG. 2 is an expanded view of the tip of the surgical knife showing the relationship of the cutting blade to the end surface of the surgical knife for the present invention.

FIG. 2 shows an expanded view of the tip of surgical knife 10 wherein the blade holding portion 14 is shown as a truncated pyramid tapering down from the cylindrical handle portion 12 toward blade 16. The pyramidal blade holding portion 14 is truncated to form end surface 18 at an acute angle 20 to the major axis of surgical knife 10. Blace 16 is placed in the mold prior to the molding procedure so that the non-sharpened edge 23 of blade 16 is substantially parallel to the major axis of surgical knife 10 to provide good visibility of the knife blade tip 27 during surgery. In addition, blade 16 is also placed so that its side surfaces are substantially perpendicular to trailing edge 22 of end surface 18 and non-sharpened edge 23 of blade 16 being substantially mid-way between the two end portions of trailing edge 22. Further, the portion of blade 16 which extends from end surface 18 is triangular in shape with blade cutting edge 24 being its longest exposed edge.

A typical blade 16 would be made of stainless steel or some other corrosion resistant material that is capable of being sharpened. Blade cutting edge 24 is shown forming an acute angle with non-sharpened edge 23 with these two edges meeting in blade tip 27. This configuration allows for easy tissue entry at an exact and visible location. A blade for this type of instrument would also typically be approximately 0.1 to 0.15 millimeters thick to allow for a fine incision which is not as wide as the incision is deep. Surgical knife 10 can be constructed in several different ways. Blade 16, blade holding portion 14 and handle portion 12 can be manufactured by insert molding or alternately by joining blade 16 to blade holding portion 14 by suitable adhesive, ultrasound or other well known techniques. By any of these approaches the protrusion length of blade 16 from blade holding portion 14 can be precisionally determined and set at the time of manufacture. Using this approach a selection of knives each with a different cutting depth could be made available very inexpensively thus eliminating a cumbersome and time consuming job of adjusting the exposure of the cutting tip with knives that are currently available.

By setting blade 16 into blade holding portion 14 in the manner described above, i.e., with the non-sharpened edge 23 of blade 16 located substantially in the center of trailing edge 22, there is a built-in guide surface to prevent blade holding portion 14 from following blade 16 into the incision. This is accomplished by the combination of end surface 18 which is initially brought into substantially direct contact with the surface in which the incision is to be made and as the knife is drawn toward the surgeon, trailing edge 22 becomes a pivot point which is wide enough to provide lateral support for the blade holding portion 14 to minimize the tendency of the blade holding portion 14 to follow blade 16 into the incision yet short enough to allow good visualization of the blade and the surface being cut during the surgery.

Figure 3:
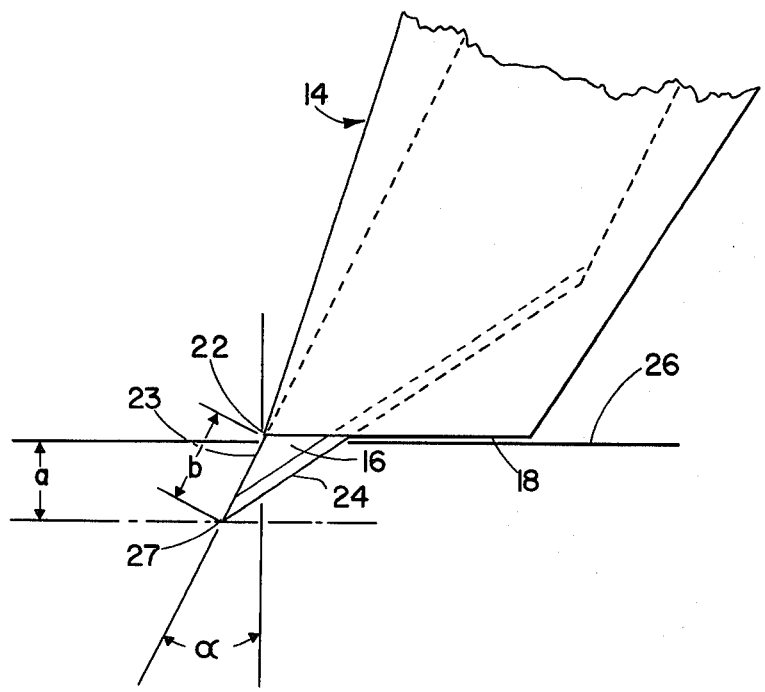
FIG. 3 is a plane side view illustrating the dimensional and angular relationships between the cutting surface, the tip of the surgical knife and the cutting blade.

In FIG. 3, blade 16 is shown relative to end surface 18 of blade holding portion 14. It can be seen that the non-sharpened edge 23 of blade 16 is substantially parallel to the major axis of surgical knife 10. In addition, end surface 18 of the blade holding portion 14 is angled such that when end surface 18 is substantially parallel to tissue surface 26, the non-sharpened edge 23 of knife 16 forms an angle $\alpha$ with a line perpendicular to tissue surface 26. Thus, it can further be seen that end surface 18 controls the initial depth of cut a, and in addition provides the initial orientation of surgical knife 10 to the tissue surface 26 in which the incision is to be made.

Figure 4A:
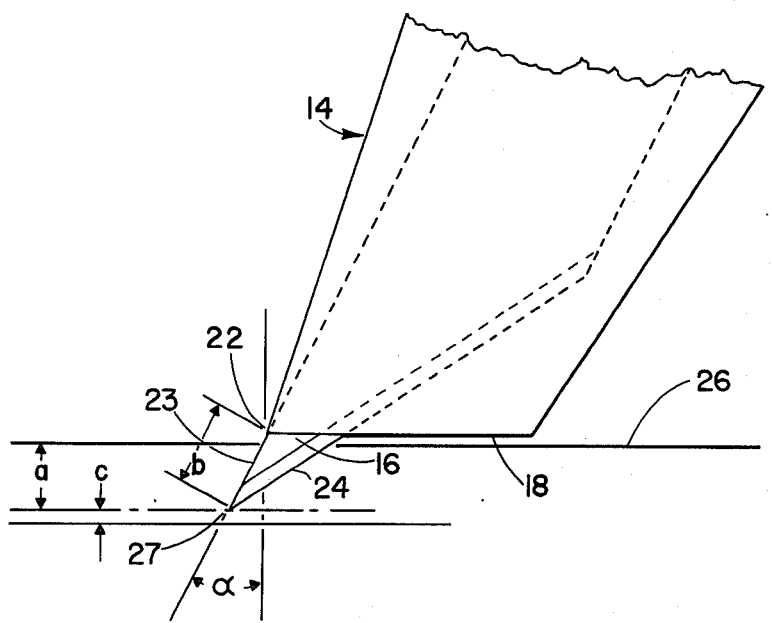
FIGS. 4A through 4C are plane side views of the tip of the surgical knife of the present invention in which the controlled cutting depth feature is illustrated with the handle of the knife at three different angles with respect to the cutting surface.
Figure 4B:
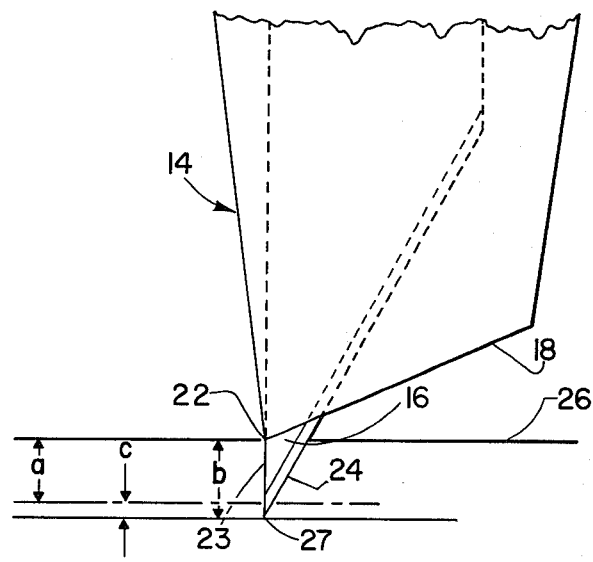
Figure 4C:
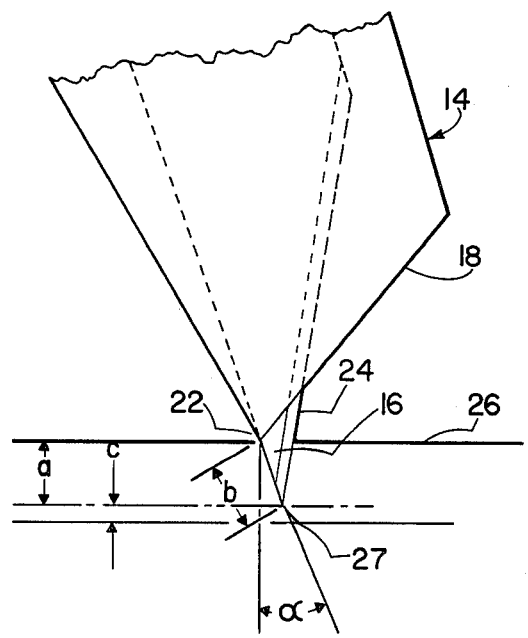

FIGS. 4A through 4C illustrate how the depth of cut varies as the surgeon draws surgical knife 10 toward him as he makes the incision. In FIG. 4A the position of surgical knife 10 shown in FIG. 3 just after blade 16 has been inserted through tissue surface 26 has been repeated. In this view blade 16 extends to a vertical depth a. In FIG. 4B surgical knife 10 is shown as having been drawn toward the surgeon and rotated about trailing edge 22 (i.e., trailing edge 22 of end surface 18 remains in contact with tissue surface 26 as the balance of end surface 18 is rotated away from tissue surface 26) with the major axis of surgical knife 10 now being substantially perpendicular to tissue surface 26. In this view, blade 16 is shown making a cut of b in depth, the maximum depth of cut possible. It should be noted at this point that b is the exposed length of the non-sharpened edge 23 of blade 16.

Finally, in FIG. 4C surgical knife 10 is shown having been drawn yet closer to the surgeon and thus rotated past the maximum depth cut position shown in FIG. 4B with the non-sharpened edge 23 of blade 16 now forming an angle $\alpha$ with respect to a perpendicular to tissue surface 26 on the opposite side of the vertical from that shown in FIG. 4A.

In FIGS. 4A through 4C, we have shown the probable full extent of the surgeon's drawing the knife toward him and pivoting the knife about trailing edge 22 in most surgical procedures. Thus the depth of cut variation produced in using a knife of the type of the present invention in the manner disclosed will be the difference between depth a as shown in FIGS. 4A and 4C, and depth b shown in FIG. 4B with that difference between these two depths of cut being c. From the geometry of surgical knife 10 it can be seen that the minimum incision depth a is directly related to the angle $\alpha$. This relationship can be expressed as $a = b (\cos \alpha)$ wherein b is the exposed length of the non-sharpened edge 23 of blade 16.

From the geometry of surgical knife 10 we can see that for a large angle $\alpha$ the surgeon will have a greater degree of flexibility in positioning of the knife than if the angle $\alpha$ is smaller; however, the depth of cut with a large angle $\alpha$ will be less uniform than with a smaller angle $\alpha$. Therefore, it is desirable that the surgical knife 10 be designed with an angle $\alpha$ that is large enough to allow a reasonable degree of flexibility in the angle at which the knife is held but yet a small enough angle $\alpha$ to provide a relatively uniform depth of cut. For example, in eye surgery it is desirable to have a controlled depth of cut on the order of 0.5 millimeters. Thus, if angle $\alpha$ is 25° a maximum depth of cut b, that is the exposed length of the non-sharpened edge 23 of blade 16, would be selected to be 0.5 millimeters. In this situation, the minimum depth of cut a would be b (COS 25°) = 0.5 × 0.906 = 0.45 millimeters. Thus we can see that with an angle $\alpha$ of 25° the surgeon could draw surgical knife 10 through a 50° arc as shown in FIGS. 4A through 4C with a depth of cut varying no more than 10%. This relatively uniform depth of cut is in contrast to that achieved with the prior art knives discussed in the background where drawing of the surgical knife through a 50° arc can cause up to a 500% variation in the depth of cut.

From the foregoing description, it will be apparent that the invention disclosed herein provides a novel and advantageous surgical knife design. As will be understood by those familiar with the art, the invention may be embodied in other specific forms without departing from the spirit or essential characteristics thereof.

I claim:

1. A surgical knife for making incisions of a controlled depth in a selected tissue surface comprising:
   handle means for controlling the movements of the knife having a tapered end, said tapered end being selectively truncated obliquely to the major axis of the handle means to form a substantially flat guard surface with a rectilinear edge and with a normal vector to said guard surface forming an angle $\alpha$ to the major axis of the handle means; and
   a planar blade having a dull edge and a sharpened edge, said blade being affixable substantially perpendicularly to the guard surface to extend outward therefrom with the dull blade edge normally intersecting said rectilinear edge of the guard surface with an obtuse included angle defined by the dull blade edge and the guard surface, the dull blade edge aligned to be substantially parallel to the major axis of the handle means, and the intersection of the dull and sharpened edges of the blade forming an acute included angle and defining the point of maximum extent from the guard surface with the sharpened blade edge intersecting the guard surface in an acute included angle defined by the sharpened blade edge and the forward portion of that surface with respect to the guard edge, and the portions of said rectilinear edge extending laterally from at least one side of the blade to form a guard edge for limiting the depth of the incision as the knife is pivoted about the guard edge as the knife is drawn toward the user with the guard edge being maintained against the surface to be cut.

2. A surgical knife as in claim 1 wherein said guard surface limits the depth of the initial cut without following the blade into the incision and orients the user to hold the surgical knife with its major axis at the angle $\alpha$ to a normal to the surface to be cut to provide improved visibility of the point of entry of the blade into the surface to be cut.

3. A surgical knife as in claim 2 wherein:
   the maximum depth of cut is substantially the exposed length of the dull edge of the blade; and
   the minimum depth of cut is substantially the length of the dull edge of the blade times the cosine of the angle $\alpha$.

4. A surgical knife as in claim 3 wherein said angle $\alpha$ is selected to be substantially equal to 25° with the resultant difference between said maximum and minimum depths of cut being substantially equal to 0.1 times the length of the dull edge of the blade.

* * * * *